United States Patent [19]

Crozier et al.

[11] Patent Number: 5,394,730
[45] Date of Patent: Mar. 7, 1995

[54] METHOD AND APPARATUS FOR GENERATING A VAPOR/GAS MIXTURE, AND USES THEREFOR

[75] Inventors: David Crozier; James J. Kelley, both of Indianapolis; Charles E. Stevenson, Mooresville, all of Ind.

[73] Assignee: Eli Lily and Company, Indianapolis, Ind.

[21] Appl. No.: 11,161

[22] Filed: Jan. 29, 1993

[51] Int. Cl.[6] .............................................. G01N 1/22
[52] U.S. Cl. ...................................................... 73/1-G
[58] Field of Search ..................... 73/1 G; 436/9, 179; 137/7, 896, 897; 356/243; 250/252.1 R; 261/65

[56] References Cited

U.S. PATENT DOCUMENTS

| | | | |
|---|---|---|---|
| 3,618,363 | 11/1971 | Kraus | 73/1 G |
| 4,349,358 | 9/1982 | Tarancon | 137/7 |
| 4,723,436 | 2/1988 | Moreth et al. | 73/1 G |
| 5,239,856 | 8/1993 | Mettes et al. | 73/1 G |

FOREIGN PATENT DOCUMENTS 0711431  1/1980  U.S.S.R. ................................. 436/9

*Primary Examiner*—Robert Raevis
*Attorney, Agent, or Firm*—Woodard, Emhardt, Naughton, Moriarty & McNett

[57] ABSTRACT

A method and apparatus for generating a vapor/gas mixture includes storing a plurality of volatile liquids to provide the vapor component of the mixture, adding predetermined amounts of the volatile liquids and a dilution gas to a container, and thereafter removing the mixture to prepare a second vapor/gas mixture. In one approach, subsequent mixtures are prepared using different volatile liquids as the vapor component. Alternatively, a portion on the first vapor/gas mixture is removed from the container and then additional volatile liquid or dilution gas are added to the container to prepare a second vapor/gas mixture including the same vapor but at a different percentage in the mixture, or including additional vapors not used in the first vapor/gas mixture.

12 Claims, 4 Drawing Sheets

METHOD AND APPARATUS FOR GENERATING A VAPOR/GAS MIXTURE, AND USES THEREFOR

BACKGROUND OF THE INVENTION

1. Field of the Invention

The present invention relates to methods and apparatus for producing vapor/gas mixtures, and more particularly to the production of mixtures containing different vapors and at various concentrations.

2. Description of the Prior Art

Gas phase analyzers are used for many applications including the analysis of gas emissions generated in various chemical processes, and are particularly useful for monitoring compliance with environmental regulations. These gas phase analyzers must be calibrated, requiring the generation of mixtures of the vapor(s) to be monitored in a dilution gas with precise concentrations.

By current methods, production of the requisite vapor/gas mixtures, and therefore the subsequent calibration of analytical instrumentation using such mixtures, is expensive, fraught with hazards, and not entirely satisfactory. For example, commercially available, custom mixtures of gases containing known quantities of a vapor or gas to be analyzed by a gas phase analyzer are contained in very heavy cylinders which must be secured and which are difficult to transport. Further, only a few of the volatile compounds used in industry are available as custom mixtures, either because of toxicity, danger of condensation at the desired concentration, or unfavorable economics. Also, the accuracy and/or stability of such mixtures has been problematic. Moreover, when many volatile compounds are to be monitored, a separate tank or container is required for each compound, a regulator is required for each tank, and a manifold is required to introduce the appropriate mixture into the analyzer. Vapor/gas mixtures suitable for calibrating gas phase analyzers available at low concentration, in the order of parts per million concentrations, are often generated from high concentration mixtures using gas blending equipment. The high concentration mixtures used in this method have the same requirements and suffer the same problems as mentioned above, and there is an additional expense in the purchase of the blending equipment. An alternative to storing the needed vapor/gas mixtures in cylinders is to generate the mixtures dynamically when they are needed. Diffusion tube and permeation tube generators are very accurate and many solvent mixtures of interest can be generated. The concentration range which can be generated is from parts per billion to high parts per million, depending on the characteristics of the volatile compound, the oven temperature, and the flow rate of the dilution gas. Unfortunately, diffusion and permeation tube calibrators are not automated and thus are labor intensive, do not accommodate more than a few volatile compounds, and cannot generate concentrations in the percent range which is frequently desired in certain process and environmental analyses.

Vapor/gas mixtures are also produced in the prior art by bubbling a gas through a liquid. If the system is well designed, and the temperature and pressure of the system are well controlled, a mixture of the vaporous compound, at its vapor pressure, and the gas is generated. The bubbler method can be automated fairly easily, but the temperature must be very accurately controlled and the concentrations produced can vary over a wide range for solvents of slightly different boiling points. Only one concentration can be produced, and for typical solvents the concentration is quite high.

Highly accurate concentrations of vapor/gas mixtures are also commonly prepared by introducing a measured mass of volatile compound into an inert enclosure, and then adding an inert gas to the vapor until the desired final total pressure is obtained. Since an accurate automated method for measuring and transferring a small mass liquid is not available, this method is not suitable for an automated vapor/gas generator. Commercial vapor/gas mixture vendors prepare mixtures in essentially this manner. A measured mass or volume of the solvent of interest is injected into a cylinder and then the cylinder is filled with permanent, dilution gas to a final measured pressure and temperature.

What is desired is a method to produce accurate, custom vapor/gas mixtures on demand, without the need to change, store, or transfer large gas cylinders.

SUMMARY OF THE INVENTION

An object of the invention is to provide an apparatus and method for generating vapor/gas mixtures, and in particular foe providing vapor/gas mixtures of known concentration which are accurate and relatively easy to generate.

Another object is to provide vapor/gas mixtures suitable for a variety of purposes, such as calibrating gas phase analyzers. An apparatus and method for generating different concentrations of a plurality of different compounds is also provided, many of which compounds are not commercially available in suitable mixtures, but which are present in emissions of commercial chemical processes and are environmentally significant.

The present invention provides a means for automating and reducing the size of systems used to generate customized vapor/gas mixtures. A predetermined quantity of the volatile liquid(s) of interest is introduced into a fixed volume container. In the preferred embodiment, the compound is introduced in liquid form and caused to evaporate within the container, which in the preferred embodiment is a modified stainless steel sample vessel. A permanent, dilution gas is added to the fixed volume until the total pressure reaches a predetermined value. The vapor to be analyzed or used in the calibration or other application and the permanent gas are allowed to mix, yielding the desired vapor/gas mixture.

In one application, for example, the mixture is vented to the inlet of an analyzer. In any event, the mixture remaining in the fixed volume container can be diluted accurately with an additional amount of the dilution gas multiple times, producing mixtures of the vapor and dilution gas with a wide range of vapor concentrations.

The desired apparatus for generating vapor/gas mixtures comprises a means, such as an automatic liquid sampler, for storing a plurality of compounds to be analyzed by said analyzer, and means for separately storing a permanent, dilution gas. The dilution gas and a selected one of the compounds are mixed in a mixing means such as a fixed volume container. Means are provided for automatically selecting a compound from the plurality of different compounds that are stored in the storage means. The selected compound is injected into the container, and allowed to vaporize. The dilution gas is added until the gas and vapor reach a predetermined pressure, at which time the addition of dilution gas is stopped. The apparatus also comprises means for removing substantially all of the vapor/gas mixture from the fixed volume container, so that other stored compounds, one at a time, can be selected from the storage means and introduced into the container with dilution gas.

In the preferred embodiment, the mixing means comprises a fixed volume container which includes a first input port coupled through a valve to the storage means; a second input port coupled through a valve to the supply of dilution gas; and an output port which may be coupled to an auxiliary device, such as an analyzer. A vacuum source is provided which is coupled through a valve to another port on the fixed volume container. The vacuum source is used to remove residual vapor/gas mixture from the container so that subsequent vapor/gas mixtures can be prepared without contamination from previously prepared mixtures. The sequence of valve operation for the removal of vapor/gas from the container is provided in more detail in the Description of the Preferred Embodiment.

DESCRIPTION OF THE PREFERRED EMBODIMENT

Figure 1:
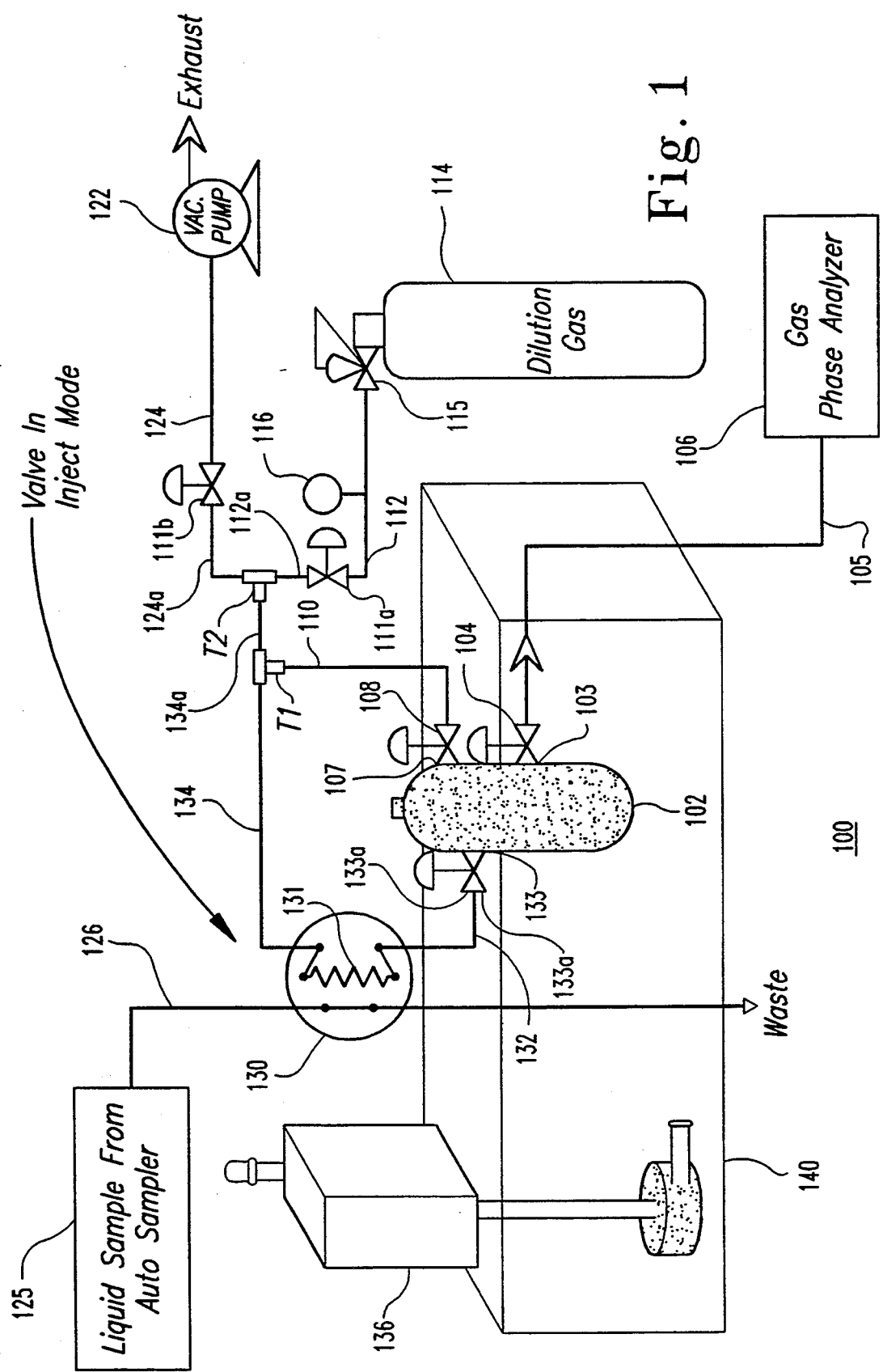
FIG. 1 is a block diagram schematic of one embodiment of the present invention.

For the purposes of promoting an understanding of the principles of the invention, reference will now be made to the embodiment illustrated in the drawings and specific language will be used to describe the same. It will nevertheless be understood that no limitation of the scope of the invention is thereby intended, such alterations and further modifications in the illustrated device, and such further applications of the principles of the invention as illustrated therein being contemplated as would normally occur to one skilled in the art to which the invention relates.

The present invention provides a system for preparing vapor/gas mixtures at a variety of predetermined ratios. Moreover, the invention facilitates the preparation of vapor/gas mixtures using different compounds as the vapor component, either singly in succession, or in combination in the same mixture. The apparatus of the invention comprises means for storing one or more volatile liquids to constitute the vapor, as well as at least one permanent, dilution gas for admixture with the vapor component. The apparatus provides for the introduction into a container of a predetermined quantity of a selected volatile liquid, which forms a vapor within the container. The dilution gas is then added to the container and intermixed with the vapor. By controlling the final pressure within the container, and/or by varying the quantity of selected volatile liquid introduced into the container, a vapor/gas mixture of desired ratio is obtained.

Further, a portion of this initial mixture can be removed from the container and the introduction into the container of more dilution gas yields a second vapor/gas mixture having a lower percentage of the vapor than for the initial mixture. As a variation of the latter approach, additional volatile liquid, of either the same composition as that used to make the initial mixture, or of a different composition, is admitted to the initial mixture, thus obtaining a mixture with a higher percentage of vapor than the initial mixture or a mixture of multiple vapors and the dilution gas.

The method produces vapor/gas mixtures in a concentration range useful for calibration and testing of many analyzers, including, mass spectrometers, gas chromatographs, infrared analyzers, combustible vapor sensors, and other gas phase analysis instruments. By way of example, applications of the gas phase analyzers for which this calibration generation method will be useful include ambient air monitoring for SARA Title III reporting, point source emissions monitoring, solvent dryer monitoring, and monitoring of fuel/oxidizer ratios in incinerator feed streams among others. The advantages of this system include compactness, portability, the ability to select mixtures of a broad range of compounds, the ability to generate standards over a broad range of concentrations for a particular solvent, the ability to produce mixtures of multiple vapors with permanent gas, the ability to conveniently change the permanent gas, and cost savings.

Referring now to FIG. 1, a block diagram schematic of an apparatus 100 for mixing a sample compound with a dilution gas in a precise concentration, useful for example for calibrating a gas phase analyzer, is disclosed. It comprises a fixed volume vessel 102 having an output port 103 with a valve 104 for removal of a prepared vapor/gas mixture from the container. In one embodiment, the interior of the vessel 102 is coupled via line 105 to a gas phase analyzer 106.

A second port 107 with a valve 108 is coupled via line 110 to a tee T1 which in turn is coupled via line 134a to a second tee, T2. One port of T2 is coupled via line 112a to a valve 111a, which in turn is connected via line 112 to dilution gas container 114. Pressure regulator 115 is mounted to container 114 to control the passage of the dilution gas through line 112, and a pressure gauge 116 is coupled to the line 112. Also coupled to T2 is the vacuum pump 122 via line 124, valve 111b and line 124a.

The apparatus 100 includes storage means for separately storing a plurality of volatile liquids available to constitute the vapor component of the vapor/gas mixtures. For example, an auto sampler 125, such as Model No. 728 available from Alcott Chromatography of Norcross, Ga., or an equivalent, is able to store a plurality of compounds of interest in liquid form. The auto sampler 125 is adapted to provide a sample of a selected compound upon external command. The sample is provided in liquid form through line 126 to valve 130. Either integral within or external to valve 130 is sample loop 131, a length of tubing whose internal volume is accurately known. Valve 130 is coupled via line 132 to an input port 133 of container 102 via valve 133a and provides a predetermined amount of the selected sample for injection into the container 102. The valve 130 is also coupled via line 134 to T1.

The apparatus preferably includes means for maintaining the contents of the container 102 at a constant temperature. In one embodiment, a fluid bath 140 containing water, oil or other suitable fluid is provided. Container 102 is at least partially immersed in the fluid bath. In an alternate embodiment, which provides portability, the temperature is maintained through use of an electrical heating element, temperature controller and temperature sensor. The temperature of the fluid bath is maintained constant by heater 136 which can control the temperature of the bath to within one degree, for example, at 54° C.

The system 100 operates in the following manner. First, the container 102 is evacuated of any prior sample gases or vapors. All valves are closed. Valves 111a and 108 are opened, which allows the container 102 to be filled and pressurized with the dilution gas, e.g., helium, argon, nitrogen, dry air or other inert gas, from the container 114. The pressure in vessel 102 is controlled by the pressure controller 115.

Valve 108 is then closed and valve 104 is opened, allowing the container 102 to vent. Valve 111a is closed and valve 111b opened to couple the vacuum source 122 to the vessel 102. Valve 104 is closed and valve 108 is opened. This allows the vessel 102 to be evacuated. Valve 111b is closed and valve 111a opened to couple dilution gas in container 114 with open value 108, and the vessel is again pressurized. The operation of closing valve 108, opening valve 104 to vent the vessel 102, and then switching valve 111b to the vacuum source 122 and closing valve 104 and opening valve 108 to evacuate the vessel is repeated two more times. Finally, after venting the vessel by closing valve 108 and opening valve 104, valves 111a and 111b are closed, valve 133a is opened to vent lines 132, 131, 134, 110, 134a, 112a, and 1124a. All valves are closed and the vessel is then in a condition ready to accept injection of the sample liquid from the auto sampler 125.

The liquid whose vapor is desired is selected in the storage device 125. Valve 130 is put into its "load" position. The selected liquid is caused to flow from storage device 125 through line 126, through the sample loop 131 and then to waste. The valve 130 is switched to its alternate "inject" position. Valves 111a and 133a are opened so that dilution gas flows from tank 114, through lines 112, 112a, 134a, 134, and 132, and through the sample loop 131 into container 102, thereby displacing the volatile liquid contained in the sample loop 131 and transporting it into container 102. The permanent dilution gas is added to the vessel until the final total pressure in the vessel 102 is equal to regulated pressure set by regulator 115, and then valve 133a is closed. The vapor and gas within the vessel are allowed to mix. The exact concentration of volatile compound in the vapor/gas mixture is determinable using the ideal gas law wherein it is assumed (1) that the liquid volatile compound introduced in the vessel undergoes complete evaporation, (2) that the volume of the vessel, the final pressure and temperature, and the volume and density of the volatile liquid introduced are well known, and (3) that significant adsorption of the volatile compound on the surface of tile vessel does not occur.

In one example, reagent grade acetone (Mallinkrodt) and ultra high purity helium gas (Mallinkrodt) were used. The evaporation vessel was a modified Whitey stainless steel sample cylinder having a nominal volume of one liter. The temperature of the vessel and its contents was controlled using a water bath and the pressure gauge was a Bourdon tube gauge. The vacuum was supplied by a two stage rotary mechanical pump. After the gases were well mixed, the exhaust valve 104 was opened, venting the mixture to atmosphere and to a gas phase analyzer where analysis of the mixture by gas chromatography was started.

The vapor/gas mixture in the vessel was assumed to behave as an ideal gas. The concentration (C) of the solvent vapor in the vapor/gas mixture, in percent, is defined as the ratio of the partial pressure if the vapor ($P_v$), in $N/m^2$ to the total pressure ($P_t$) of the system, in $N/m^2$ times 100. The total pressure of the system was estimated from the reading on the gas supply gauge 116. The partial pressure of the vapor was derived assuming that the injected liquid was completely evaporated and that the vapor behaved as an ideal gas. The concentration of vapor was defined to be:

$$C(ppm) = P_v/P_t \times 10^2$$

The partial pressure of the solvent is calculated as:

$$P_v = \frac{nR(T + 273)}{V}$$

in which n=the gmoles of the compound injected (gmole); R=the Universal Gas Constant (8.314 J/gmole/° K); T=the temperature of the gas in the vessel (° C.); and V=the volume of the mixing vessel ($m^3$). The number of moles of volatile liquid injected is:

$$n = vr/f$$

in which v=the volume of the solvent: injected ($cm^3$); r=the solvent density ($gm/cm^3$); and f=the molecular weight of the solvent (gm/gmole). The volume of tile vessel was estimated to be 1.01 liters by measuring the volume of water added to the vessel to fill it. For V equal to 1.01 L, $$C = (1.192 \times 10^2) \frac{vr}{f} \cdot \frac{T + 273}{P_g + 14.3}$$

Values of density (r) and molecular weight (f) for acetone as well as other solvents of particular interest are given in Table 1.

TABLE 1

| SOLVENT | MOLECULAR WEIGHT (g/g mole) | DENSITY (g/cm³) |
|---|---|---|
| ACETONE | 58.08 | 0.7908 |
| AMYL ALCOHOL | 88.15 | 0.811 |
| N,N-DIMETHYLFORMAMIDE | 73.15 | 0.944 |
| ETHANOL | 46.07 | 0.7893 |
| ETHYL ACETATE | 88.11 | 0.9005 |
| ETHYLENE DICHLORIDE | 98.96 | 1.256 |
| HEXANE | 86.16 | 0.659 |
| ISOAMYL ALCOHOL | 100.18 | 0.8205 |
| ISOPROPANOL | 60.09 | 0.7851 |
| METHANOL | 32.04 | 0.7914 |
| METHYLENE CHLORIDE | 84.93 | 1.335 |
| PYRIDINE | 79.1 | 0.9819 |
| TOLUENE | 92.13 | 0.8669 |

Figure 2:
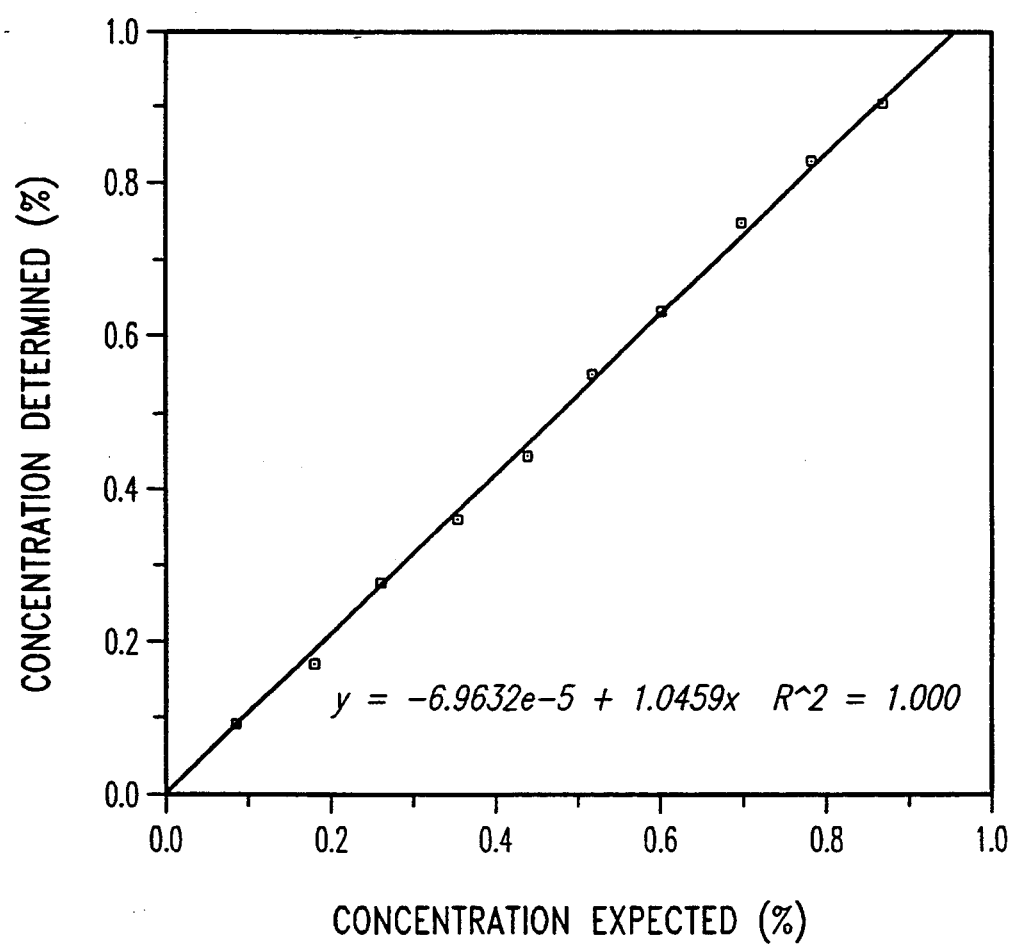
FIG. 2 is a graph showing the measured concentration of a sample compound in the vapor/gas mixture versus the calculated concentration from the ideal gas law.

Volumes of acetone were injected into the vessel and the mixtures analyzed as described above. Two injections were made at different sets of volumes. The gas chromatography peak area increased linearly with volume. As shown in FIG. 2, the plot of the concentration determined from the gas chromatography measurement against the expected concentration based on the foregoing calculation revealed a slight bias (slope=1.0459). This bias might be attributed to non-ideality, to inaccuracy in commercially obtained mixtures used to calibrate the gas chromatograph used to determine the concentration of vapor in the mixtures, or to other systematic error or errors in tile analytical system. Because of the excellent linearity of the relationship in the concentration range examined, tile cause is not likely to be non-ideality.

Figure 3:
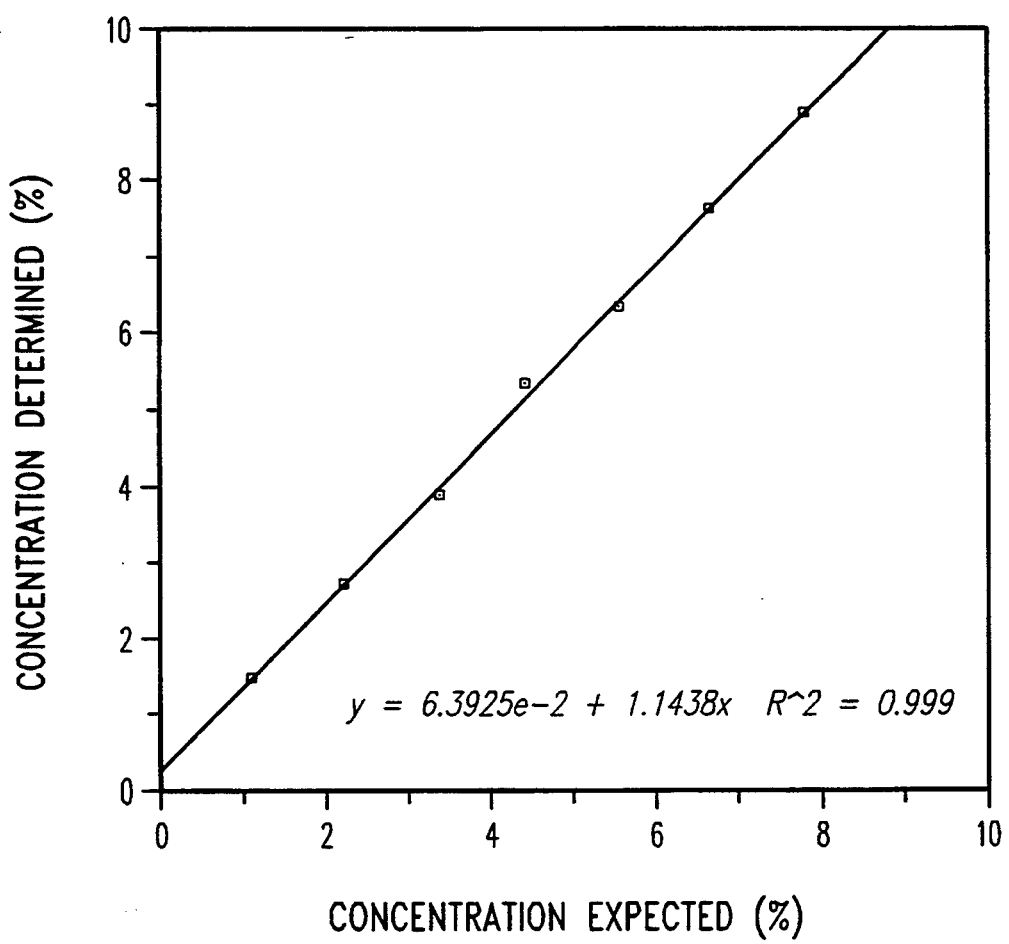
FIG. 3 is a similar graph to that of FIG. 2 for a different compound.

The above described apparatus and method were demonstrated to be able to produce vapor/gas mixtures which have acceptable accuracy, precision and linearity in a broad range, e.g. 0.05–10%. Similar measurements were made for ethanol, and the plot of measured concentration versus calculated concentration is shown in FIG. 3.

It will be appreciated that the foregoing method permits the preparation of an initial vapor/gas mixture having a predetermined percentage of vapor of a selected volatile liquid. This process is repeatable for any of the stored volatile liquids. In addition, mixtures of a particular volatile liquid having different percentages of a single vapor are also readily prepared. The first such vapor/gas mixture is prepared in accordance with the foregoing description. A portion of this first vapor/gas mixture is then removed from the container, such as by venting the container to a predetermined pressure. The foregoing steps are then repeated to admit additional dilution gas into the container, thus forming a second vapor/gas mixture having a different ratio of vapor than the first mixture. This process may be repeated to produce mixtures having progressively lower concentrations of the vapor.

Figure 4:
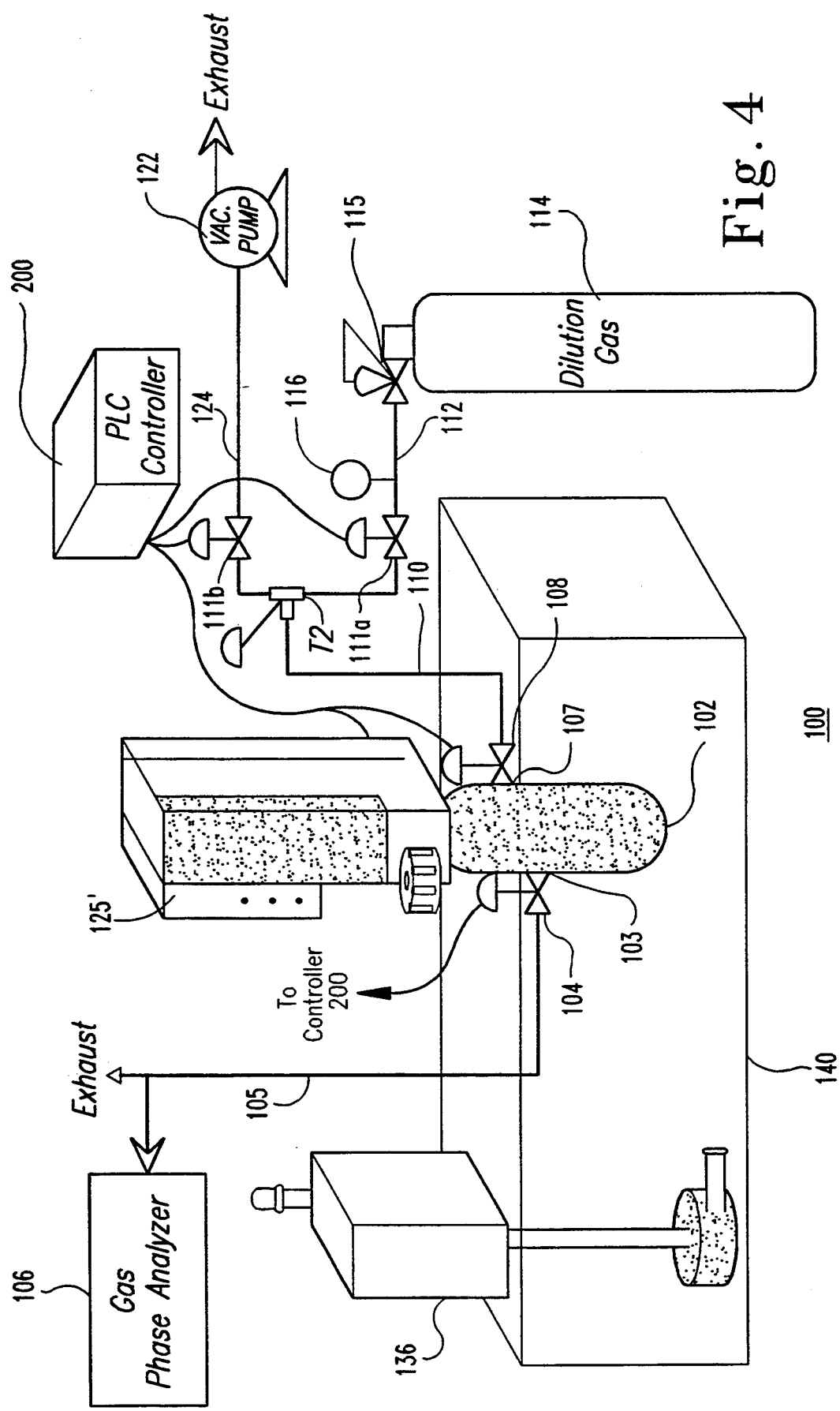
FIG. 4 is a block diagram schematic of an alternate embodiment of the present invention.

FIG. 4 shows an alternate embodiment of the system. Those components which are the same as those shown in FIG. 1 are similarly labelled. Instead of the auto sampler 125 being coupled through a rotary valve, an auto injector 125' of the variety commonly used in gas chromatography, such as Model 7673 by Hewlett Packard, is shown coupled directly to the cylinder 102. A controller 200 is added and is shown coupled to the sampler and the three valves 104, 108 and 111. The controller 200, such as a programmable logic controller, can be programmed in a manner well known to those skilled in the art to control selection of the samples and the opening and closing of the valves in accordance with the description provided above, in order to operate the apparatus and perform the method disclosed in this invention.

While tile invention has been illustrated and described in detail in the drawings and foregoing description, the same is to be considered as illustrative and not restrictive in character, it being understood that only the preferred embodiment has been shown and described and that all changes and modifications that come within the spirit of tile invention are desired to be protected.

What is claimed is:

1. An apparatus for generating a vapor/gas mixture of predetermined composition which comprises:
    storage means for separately storing a plurality of different volatile liquid compounds, said liquid compounds to constitute the vapor of the vapor/gas mixture, said storage means comprising an auto sampler which includes means for storing a plurality of volatile liquids;
    means for providing a dilution gas;
    a mixing container;
    introduction means for automatically introducing a predetermined quantity of at least a selected one of the plurality of volatile liquids from said storage means into said container, the predetermined quantity forming a vapor within said container;
    means for adding the dilution gas into said container until the gas pressure in said container reaches a first predetermined pressure, thereby generating a first vapor/gas mixture of the selected volatile liquid and the dilution gas having a selected percentage of the compound therein; and
    means for removing substantially all of the first vapor/gas mixture from said container, whereby said apparatus is ready for preparing a second vapor/gas mixture using a different one of the plurality of volatile liquids.

2. The apparatus of claim 1 and which includes means for removing a portion of the first vapor/gas mixture, and in which the means for adding the dilution gas is also for adding more dilution gas to said mixing container until the gas pressure in said container reaches a second predetermined pressure, thereby generating a second vapor/gas mixture of the selected volatile liquids and the dilution gas with the percentage of selected compound being a determined percentage, less than in the first vapor/gas mixture.

3. The apparatus of claim 1 and which includes means for maintaining said container and its contents at a constant temperature.

4. The apparatus of claim 3 in which said constant temperature maintaining means comprises a fluid bath partially surrounding said container and a heater coupled to said fluid bath.

5. The apparatus of claim 1 and further including a vacuum source, said means for removing includes means for selectively coupling said container with said vacuum source.

6. The apparatus of claim 1 and which further includes means for providing the vapor/gas mixture to a gas analyzer for calibration.

7. An apparatus for generating a vapor/gas mixture of predetermined composition which comprises:
    storage means for separately storing a plurality of different volatile liquid compounds, said liquid compounds to constitute the vapor of the vapor/gas mixture;
    means for providing a dilution gas;
    a mixing container;
    introduction means for automatically introducing a predetermined quantity of at least a selected one of the plurality of volatile liquids from said storage means into said container, the predetermined quantity forming a vapor within said container, said introduction means including valve means for selectively connecting the plurality of volatile liquids with said container;
    means for adding the dilution gas into said container until the gas pressure in said container reaches a first predetermined pressure, thereby generating a first vapor/gas mixture of the selected volatile liquid and the dilution gas having a selected percentage of the compound therein; and
    means for removing substantially all of the first vapor/gas mixture from said container, whereby said apparatus is ready for preparing a second vapor/gas mixture using a different one of the plurality of volatile liquids.

8. A method for generating a plurality of vapor/gas mixtures of predetermined composition which comprises:
    a. providing means for separately storing in an auto sampler a plurality of different volatile liquid compounds to constitute the vapor of the vapor/gas mixture;

b. automatically introducing a predetermined quantity of a selected one of the plurality of volatile liquids from the storing means into a container, the predetermined quantity forming a vapor within the container;

c. adding dilution gas into the container until the gas pressure in the container reaches a first predetermined pressure, thereby generating a first vapor/gas mixture of the selected compound and the dilution gas having a selected percentage of the compound therein;

d. removing substantially all of the first vapor/gas mixture from the container; and e. repeating steps b. through d. using a different one of the plurality of stored volatile liquids to generate other vapor/gas mixtures with different ones of the volatile liquids.

9. The method of claim 8 in which for at least one compound the method includes removing a portion of the vapor/gas mixture including that volatile liquid from within the container and thereafter adding at least one of additional volatile liquid or dilution gas to the container to generate a second vapor/gas mixture which includes the same vapor as the first vapor/gas mixture but having a different percentage of the vapor therein.

10. The method of claim 8 which includes removing a portion of the vapor/gas mixture from within the container and thereafter adding an additional, predetermined amount of the dilution gas to a second predetermined pressure to produce a second vapor/gas mixture having a percentage of vapor less than in the first vapor/gas mixture.

11. The method of claim 8 and which includes maintaining the container and its contents at a constant temperature.

12. The method of claim 8 and which after step c. includes the step of analyzing the percentage composition of the vapor/gas mixture.

* * * * *